US012664615B2

(12) United States Patent
Cutforth et al.

(10) Patent No.: US 12,664,615 B2
(45) Date of Patent: Jun. 23, 2026

(54) THERMOGRAPHY IMAGE CORRECTION APPARATUS AND METHOD

(71) Applicant: CANON KABUSHIKI KAISHA, Tokyo (JP)

(72) Inventors: Murray Cutforth, Edinburgh (GB); Ewan Hemingway, Edinburgh (GB)

(73) Assignee: CANON KABUSHIKI KAISHA, Tokyo (JP)

( * ) Notice: Subject to any disclaimer, the term of this patent is extended or adjusted under 35 U.S.C. 154(b) by 535 days.

(21) Appl. No.: 18/059,063

(22) Filed: Nov. 28, 2022

(65) Prior Publication Data

US 2024/0177270 A1      May 30, 2024

(51) Int. Cl.
| | |
|---|---|
| *G06T 5/50* | (2006.01) |
| *A61B 5/01* | (2006.01) |
| *G06T 5/70* | (2024.01) |
| *G06T 7/00* | (2017.01) |
| *G06T 12/30* | (2026.01) |

(52) U.S. Cl.
CPC .............. *G06T 5/50* (2013.01); *A61B 5/015* (2013.01); *G06T 5/70* (2024.01); *G06T 7/0016* (2013.01); *G06T 12/30* (2026.01); *G06T 2207/10081* (2013.01); *G06T 2207/10088* (2013.01); *G06T 2207/20224* (2013.01); *G06T 2207/30056* (2013.01); *G06T 2207/30096* (2013.01)

(58) Field of Classification Search
CPC ....... A61B 5/0035; A61B 5/015; A61B 5/055; G06T 11/008; G06T 2207/10081; G06T 2207/10088; G06T 2207/20224; G06T 2207/30056; G06T 2207/30096; G06T 5/50; G06T 5/70; G06T 7/0016; G06T 12/30
See application file for complete search history.

(56) References Cited

U.S. PATENT DOCUMENTS

| | | | |
|---|---|---|---|
| 4,920,491 | A | 4/1990 | Eberhard et al. |
| 9,846,765 | B2 | 12/2017 | Audigier et al. |

(Continued)

FOREIGN PATENT DOCUMENTS

| | | |
|---|---|---|
| CN | 103186888 A | 7/2013 |
| CN | 103656760 A | 3/2014 |

(Continued)

OTHER PUBLICATIONS

Wang, N. et al., "Deep learning based CT thermometry for thermal tumor ablation," Proc. SPIE 11113, Developments in X-Ray Tomography XII, 111131T (Sep. 10, 2019); https://doi.org/10.1117/12.2530771 (10 pages).

(Continued)

*Primary Examiner* — Kenny A Cese
(74) *Attorney, Agent, or Firm* — Oblon, McClelland, Maier & Neustadt, L.L.P.

(57) ABSTRACT

Certain embodiments provide a medical image processing apparatus comprising processing circuitry configured to: receive a thermography image, or a pair of medical images from which a thermography image is obtainable; estimate a temperature field corresponding to the thermography image or pair of medical images; and generate a corrected thermography image based on the thermography image or pair of medical images and on the estimated temperature field.

18 Claims, 4 Drawing Sheets

(56) References Cited

U.S. PATENT DOCUMENTS

| | | | | | |
|---|---|---|---|---|---|
| 10,242,439 | B1 | 3/2019 | Koshti | | |
| 2006/0056579 | A1 | 3/2006 | Stierstorfer | | |
| 2006/0229856 | A1* | 10/2006 | Burrus | G16H 30/40 | |
| | | | | | 703/11 |
| 2007/0106157 | A1 | 5/2007 | Kaczkowski et al. | | |
| 2009/0161935 | A1 | 6/2009 | Bruder et al. | | |
| 2009/0279768 | A1 | 11/2009 | Nishikawa | | |
| 2010/0185087 | A1* | 7/2010 | Nields | A61B 6/035 | |
| | | | | | 378/4 |
| 2012/0081386 | A1* | 4/2012 | Wiemker | G06T 19/00 | |
| | | | | | 345/611 |
| 2012/0177174 | A1* | 7/2012 | Ikhlef | A61B 6/585 | |
| | | | | | 378/207 |
| 2012/0308104 | A1 | 12/2012 | Yang et al. | | |
| 2013/0336596 | A1 | 12/2013 | Toyoda et al. | | |
| 2014/0212016 | A1 | 7/2014 | Kadomura et al. | | |
| 2014/0334705 | A1 | 11/2014 | Ishii et al. | | |
| 2015/0150466 | A1* | 6/2015 | Abi-Jaoudeh | A61B 5/4839 | |
| | | | | | 600/427 |
| 2015/0348291 | A1 | 12/2015 | Kohara | | |
| 2016/0022369 | A1 | 1/2016 | Audigier et al. | | |
| 2016/0287086 | A1* | 10/2016 | Son | A61B 5/0093 | |
| 2019/0385308 | A1* | 12/2019 | Kandlikar | A61B 5/708 | |
| 2022/0036600 | A1* | 2/2022 | Cabral | G06T 7/0012 | |
| 2022/0094860 | A1* | 3/2022 | Kurihara | G06T 5/70 | |
| 2022/0196771 | A1* | 6/2022 | Zur | G01R 33/5608 | |

FOREIGN PATENT DOCUMENTS

| | | | |
|---|---|---|---|
| CN | 103961125 | A | 8/2014 |
| CN | 105321155 | A | 2/2016 |
| CN | 106157275 | A | 11/2016 |
| CN | 109472836 | A | 3/2019 |
| CN | 110400358 | A | 11/2019 |
| CN | 111882624 | A | 11/2020 |
| CN | 113069129 | A | 7/2021 |
| JP | 1-305932 | A | 12/1989 |
| JP | 2-289229 | A | 11/1990 |
| JP | 2011-156302 | A | 8/2011 |

OTHER PUBLICATIONS

Roujol, S. et al. "Robust Adaptive Extended Kalman Filtering for Real Time MR-Thermometry Guided HIFU Interventions," in IEEE Transactions on Medical Imaging, vol. 31, No. 3, pp. 533-542, Mar. 2012, doi:10.1109/TMI.2011.2171772 (11 pages).

Zachiu, C. et al. "An Adaptive Non-Local-Means Filter for Real-Time MR-Thermometry," in IEEE Transactions on Medical Imaging, vol. 36, No. 4, pp. 904-916, Apr. 2017, doi: 10.1109/TMI.2016.2627221. (13 pages).

Pohlan, J. et al. "Computed Tomography Thermography for Ablation Zone Prediction in Microwave Ablation and Cryoablation: Advantages and Challenges in an Ex Vivo Porcine Liver Model", J Comput Assist Tomogr. Sep./Oct. 2020;44(5):744-749 (6 pages).

* cited by examiner

THERMOGRAPHY IMAGE CORRECTION APPARATUS AND METHOD

FIELD

Embodiments described herein relate generally to an apparatus and method for image processing, for example for processing medical image data to generate corrected computed tomography (CT) thermography images.

BACKGROUND

It is known to obtain medical image data using computed tomography (CT) imaging. Such medical imaging data is widely used for imaging or diagnostic purposes.

CT image data may comprise a three-dimensional array of voxels. Each voxel is representative of a particular position in three-dimensional space. Each voxel has an associated intensity value that is representative of the attenuation of the applied X-ray radiation provided at the location represented by the voxel. The intensity value may be referred to as an image value, gray value, gray level, voxel value or CT value. The intensity value may be measured in Hounsfield units (HU).

It has been found that the CT intensity value in HU of a given tissue may be different at different temperatures. For example, see FIG. 4 of Pohlan et al (Pohlan, Julian MD; Kress, Wiebke; Hermann, Kay-Geert MD; Mews, Jürgen; Kroes, Maarten PhD; Hamm, Bernd MD; Diekhoff, Torsten MD. Computed Tomography Thermography for Ablation Zone Prediction in Microwave Ablation and Cryoablation: Advantages and Challenges in an Ex Vivo Porcine Liver Model. Journal of Computer Assisted Tomography: Sep. 10, 2020—Volume 44—Issue 5—p 744-749 doi: 10.1097/RCT.0000000000001081), which is hereby incorporated by reference. FIG. 4 of Pohlan et al shows a change in intensity in HU, $\Delta$HU, on a horizontal axis and a temperature difference, $\Delta$T, on a vertical axis. A larger change in temperature is associated with a larger change in HU.

CT Thermography is an imaging technique which takes advantage of the temperature dependence of HU values in order to measure volumetric temperatures using a non-invasive CT scan. In the previous decade, CT thermography has emerged as a potentially useful tool to support thermal ablation interventions, such as microwave ablation.

FIG. 1 illustrates an example of microwave ablation. A probe 10 comprising a microwave antenna 12 is inserted into a tumor 14 within a liver 16 of a patient. In use, an ablation procedure is performed in which the antenna 12 emits microwave radiation into an ablation zone 18. The microwave radiation heats tissue within the ablation zone 18. The heating of the tissue may destroy at least part of the tissue within the ablation zone.

CT thermography may be used to obtain in-vivo ablation images. To obtain a CT thermography image, a pre-ablation CT image and post-ablation CT image may be obtained for a region of a patient in which an ablation procedure is performed, for example a region corresponding to the extent of FIG. 1. Each of the pre-ablation CT image and post-ablation CT image comprises respective volumetric image data. It is expected that a pre-ablation image that is obtained before ablation takes place will be different from a post-ablation image that is obtained after ablation, for example once microwave radiation has ceased to be applied. At least part of the difference in the image will be due to the change in temperature that is caused by heating the tissue using the microwave antenna 12.

The pre-ablation CT image is registered to the post-ablation image. The registered pre-ablation CT image is then subtracted from the post-ablation image to obtain a subtraction image. The subtraction image may be considered to be representative of a difference in temperature before the ablation and temperature after the ablation.

The subtraction image is multiplied by a thermal sensitivity conversion factor to obtain volumetric temperatures. For each voxel in the subtraction image, a data value for that voxel is representative of a difference in intensity in HU between a corresponding voxel in the pre-ablation image and a corresponding voxel in the post-ablation image. By multiplying each of the voxel data values by a thermal sensitivity conversion factor, HU values may be converted to temperature values. A respective temperature value may therefore be obtained for each voxel within the subtraction image.

It has been shown that the success rate of microwave ablation procedures are highly dependent on operator experience, so there is clinical motivation to use CT thermography to support these procedures. For example, CT thermography may provide temperature information to determine whether a planned degree of heating has been obtained during an ablation procedure.

BRIEF DESCRIPTION OF THE DRAWINGS

Embodiments are now described, by way of non-limiting example, and are illustrated in the following figures, in which.

DETAILED DESCRIPTION

Certain embodiments provide a medical image processing apparatus comprising processing circuitry configured to: receive a thermography image, or a pair of medical images from which a thermography image is obtainable; estimate a temperature field corresponding to the thermography image or pair of medical images; and generate a corrected thermography image based on the thermography image or pair of medical images and on the estimated temperature field.

Certain embodiments provide a medical image processing method comprising: receiving a thermography image, or a pair of medical images from which a thermography image is obtainable; estimating a temperature field corresponding to the thermography image or pair of medical images; and generating a corrected thermography image based on the thermography image or pair of medical images and on the estimated temperature field.

Figure 2:
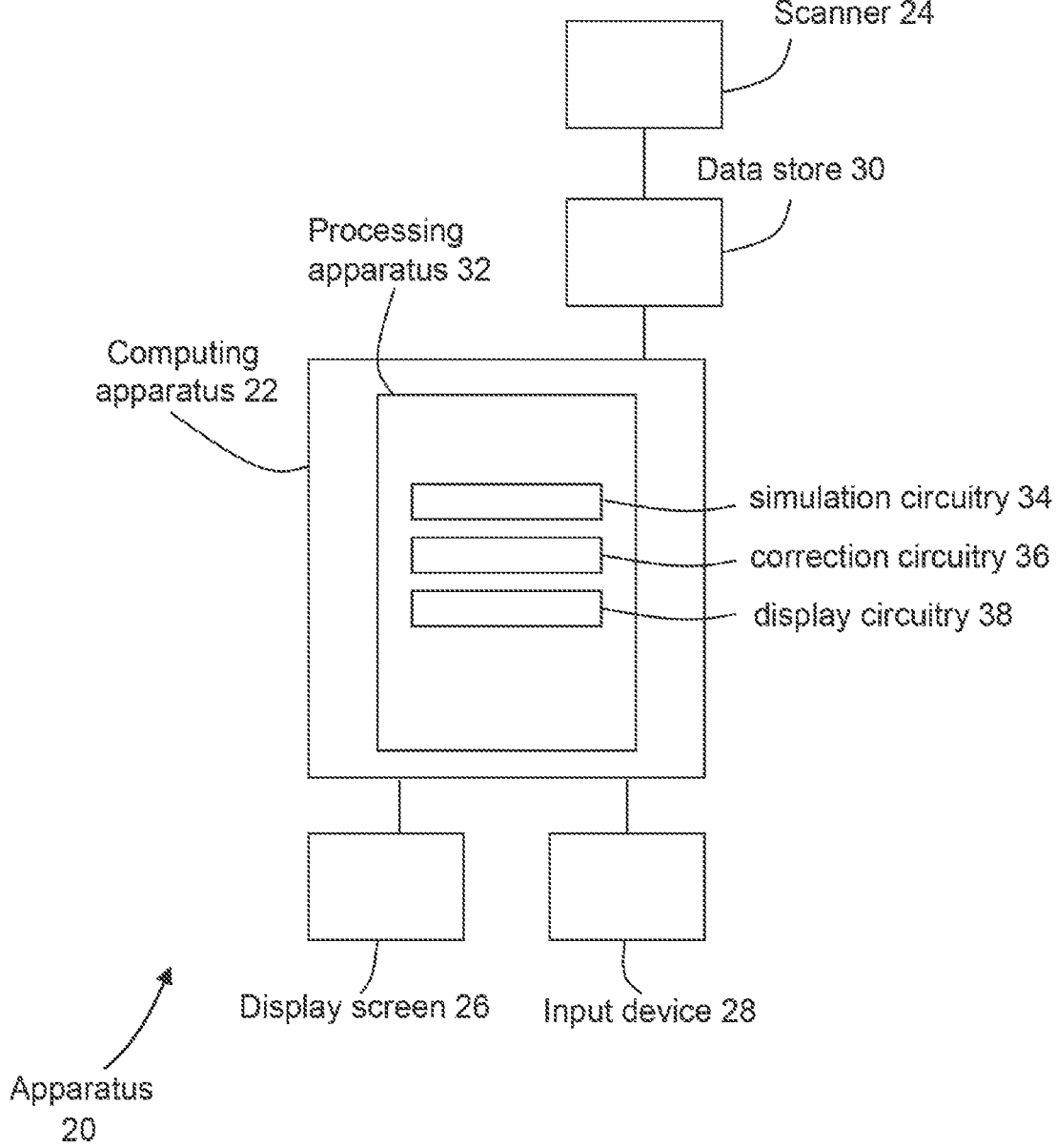
FIG. 2 is a schematic illustration of an apparatus in accordance with an embodiment.

A medical image processing apparatus 20 according to an embodiment is illustrated schematically in FIG. 2. The medical image processing apparatus 20 comprises a computing apparatus 22, in this case a personal computer (PC) or workstation, which is connected to a scanner 24 via a data store 30.

The medical image processing apparatus 20 further comprises one or more display screens 26 and an input device or devices 28, such as a computer keyboard, mouse or trackball.

In the present embodiment, the scanner 24 is a computed tomography (CT) scanner. The scanner 24 is configured to generate image data that is representative of at least one anatomical region of a patient or other subject. The image data comprises a plurality of voxels each having a corresponding data value. In the present embodiment, the data values are representative of intensity in Hounsfield units.

In other embodiments, the scanner 24 may be configured to obtain two-, three- or four-dimensional image data in any suitable imaging modality. For example, the scanner 14 may comprise a magnetic resonance (MR) scanner, computed tomography (CT) scanner or cone-beam CT scanner.

In the present embodiment, image data sets obtained by the scanner 24 are stored in data store 30 and subsequently provided to computing apparatus 22. In an alternative embodiment, image data sets are supplied from a remote data store (not shown). The data store 30 or remote data store may comprise any suitable form of memory storage. In some embodiments, the medical image processing apparatus 20 is not coupled to any scanner.

Computing apparatus 22 comprises a processing apparatus 32 for processing of data. The processing apparatus comprises a central processing unit (CPU) and Graphical Processing Unit (GPU). The processing apparatus 32 provides a processing resource for automatically or semi-automatically processing medical image data sets. In other embodiments, the data to be processed may comprise any image data, which may not be medical image data.

The processing apparatus 32 includes simulation circuitry 34 which is configured to estimate a temperature field; correction circuitry 36 which is configured to generate a corrected CT thermography image based on the estimated temperature field; and display circuitry 38 which is configured to display a corrected CT thermography image.

In the present embodiment, the circuitries 34, 36, 38 are each implemented in the CPU and/or GPU by means of a computer program having computer-readable instructions that are executable to perform the method of the embodiment. In other embodiments, the circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 2 for clarity.

Figure 3:
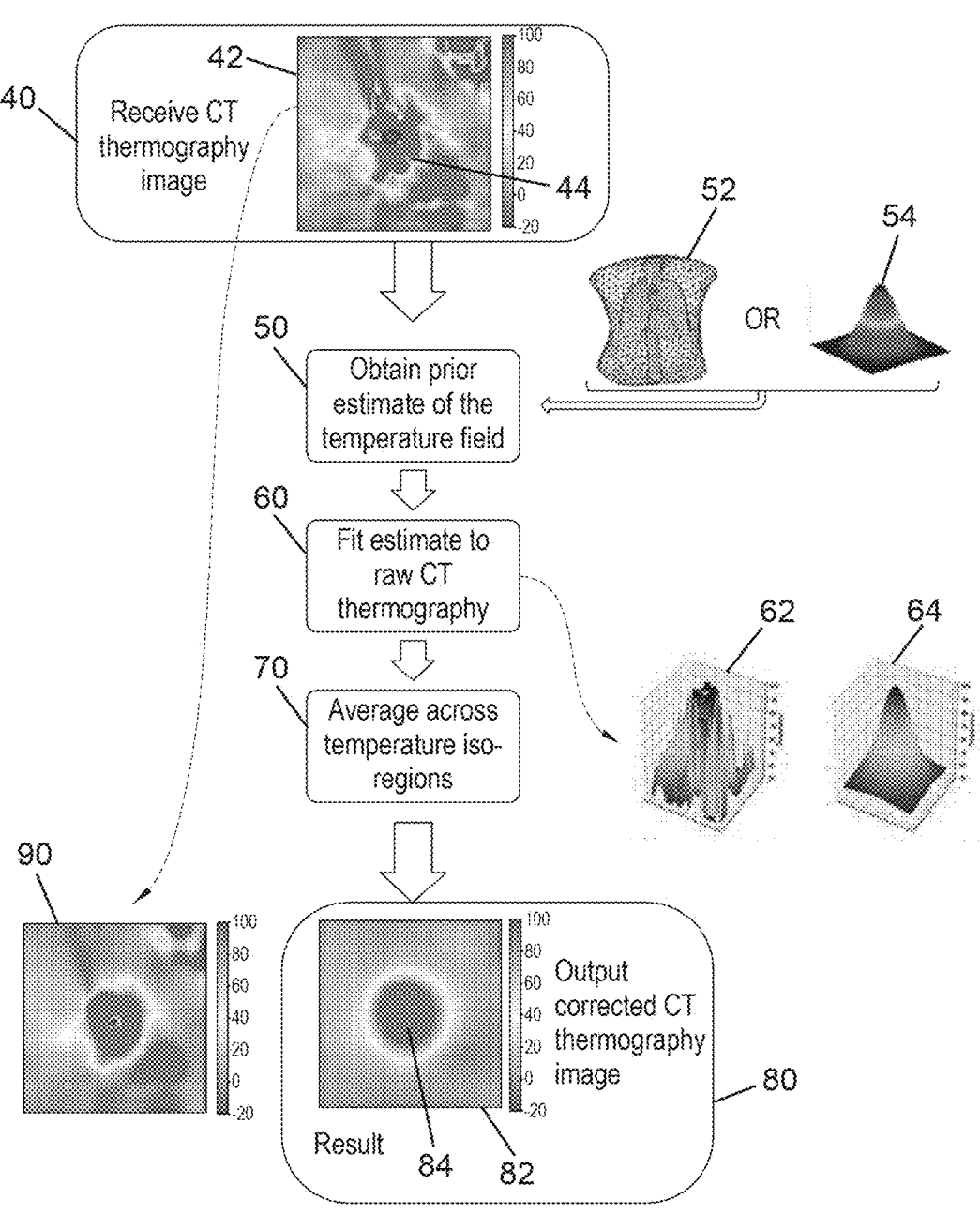
FIG. 3 is a flow chart illustrating in overview a method in accordance with an embodiment.

The apparatus 20 of FIG. 2 is configured to perform a method in accordance with FIG. 3. FIG. 3 is a flow chart illustrating in overview a method of correcting a CT thermography image by smoothing the CT thermography image.

In some circumstances, a temperature measurement that is obtained by CT thermography may be significantly impacted by imaging artefacts. Imaging artefacts may arise as a result of imperfect registration between a pre-ablation image and a post-ablation image. For example, an error in registration may cause incorrect subtraction of HU values because the voxels in the pre-ablation image are not correctly associated with corresponding voxels in the post-ablation image. Registration may be difficult when the tissue being imaged is deformable. For example, registration may be challenging in the abdominal region.

Typically, registration artefacts occur around the edges of features with large intensity gradients, such as the edges of bones or air spaces in the body. Registration artefacts may appear as outlines around the edges of features with large intensity gradients.

Alternatively or additionally, imaging artifacts that result from the presence of metal may occur around the microwave antenna 12. Such metal imaging artefacts may occur in the middle of a region of interest. Metal imaging artefacts may be caused by photon starvation and beam hardening in a metal object with very high attenuation, and may appear as dark and bright streaks emanating from the metal object.

In some circumstances, noise and/or artefacts may arise in in-vivo CT thermography imaging that have not been observed in previous ex-vivo studies. Based on observations, it is anticipated that the presence of noise and/or artefacts may present a significant barrier to routine clinical use of CT thermography if no further processing of CT thermography images is performed. Noise and artefacts in in-vivo CT thermography images may degrade, or may prevent, the use of CT thermography images in their raw form to support thermal ablation procedures.

The method of FIG. 3 provides additional processing which may improve CT thermography images, and may make them more suitable for clinical use. In the method of FIG. 3, temperature is estimated independently, and a prior estimate of temperature is used to intelligently smooth a CT thermography image. Smoothing may remove noise and/or artefacts from the CT thermography image, which may result in an image that is more useable for a clinical user.

At stage 40, the correction circuitry 36 receives a set of volumetric CT thermography data, which may also be referred to as a CT thermography image 42 or as a CT thermography measurement or set of CT thermography measurements. In the present embodiment, the CT thermography image 42 is retrieved from the data store 30. In other embodiments, the CT thermography image 42 may be retrieved from any suitable apparatus, circuitry or data store.

The CT thermography image comprises respective temperature values for each of a plurality of voxels. The CT thermography image may also be referred to as a raw thermography image, because it has not yet undergone a correction process. The CT thermography image may contain noise and/or one or more image artefacts.

Figure 1:
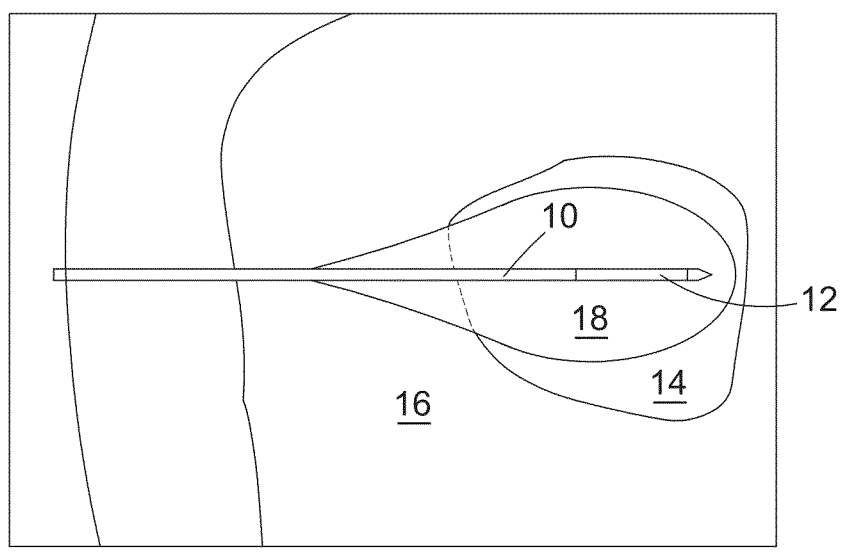
FIG. 1 is a schematic illustration of an ablation procedure.

In the embodiment of FIG. 3, the CT thermography image relates to an ablation process, for example an ablation process as illustrated in FIG. 1. The CT thermography image was generated by registering a pre-ablation image of a region of tissue of a patient to a post-ablation image of the same region of tissue of the same patient; subtracting the registered pre-ablation image and post-ablation image to obtain a subtraction image; and multiplying the subtraction image by a thermal sensitivity conversion factor to obtain volumetric temperatures. In other embodiments, the CT thermography image may be generated from any suitable pair of CT images, for example CT images obtained at different times during a medical procedure. An image obtained while thermography is ongoing may be referred to as a peri-ablation image. In some embodiments, a subtraction image may be obtained by subtracting a pre-ablation image and a peri-ablation image. In other embodiments, one or more subtraction images may be obtained by using any suitable combination or pre-, peri-, or post-ablation images.

In some embodiments, the display circuitry 28 may display a 2D image obtained from the CT thermography image to a user. For example, the 2D image may comprise a 2D slice through the 3D thermography image, or a 3D render of different temperature isosurfaces. An image obtained from the raw CT thermography image may be difficult for the user to read because of noise and/or artefacts. For example, in an example shown in FIG. 3, a heated region 44 of a CT thermography image 42 appears to have an erratic shape which may not correctly reflect a region that is heated.

At stage 50, the simulation circuitry 34 obtains an estimate of a temperature field. The estimate may also be referred to as a prior estimate. The estimate is not based on the CT thermography image.

The temperature field may also be referred to as a temperature distribution. The temperature field comprises a respective temperature value for each of a plurality of voxels, which may correspond to the voxels of the CT thermography image.

In other embodiments, the obtaining of the estimate of the temperature field may be performed before the CT thermography image is received. In some embodiments, the estimate of the temperature field may be based on one of the CT images from which the CT thermography image is formed. For example, the CT image may be used to create a mesh of blood vessel regions to be used as a boundary condition in a heat equation simulation which provides the temperature field estimate.

In the embodiment of FIG. 3, the simulation circuitry 34 receives values for one or more heating parameters relating to the ablation process. For example, the simulation circuitry 34 may receive a position of a probe 10 in a coordinate system of the CT thermography image; a power applied via the probe 10 and/or a length of time for which ablation was performed. In other embodiments, the simulation circuitry 34 may receive values for any suitable heating parameters. The heating parameters may comprise one or more parameters of the probe 10, for example one or more parameters relating to the shape or power profile of the probe or one or more parameters specifying a type of probe used. The heating parameters may comprise one or more parameters of an electric field generated by the probe. The heating parameters may comprise one more parameters relating to power deposited into the tissue, which is a function of time and space. The heating parameters may comprise one more parameters relating to a rate of heat deposition into the tissue, which is a function of time and space. The heating parameters may comprise one or more parameters relating to the tissue into which the power is applied, for example tissue types and their geometry. Parameters relating to the tissue may comprise one or more parameters relating to vasculature of the tissue, for example a vessel shape and/or one or more parameters to describe blood flow rates. Parameters relating to the tissue may be obtained from a prior scan such as the pre-ablation CT scan.

In some embodiments, default values may be used for one or more of the heating parameters, for example for power and/or time.

The simulation circuitry 34 then proceeds to either sub-stage 52 or sub-stage 54 to perform an estimating of a temperature field, thereby obtaining an estimated temperature field. The estimated temperature field is representative of expected temperature changes given the known heating parameters.

In one variant of the method of FIG. 3, stage 50 comprises sub-stage 52. At sub-stage 52, the simulation circuitry 34 performs a finite element simulation to solve a forward heat diffusion equation in the human body. The finite element simulation may be based on the values for the heating parameters received at stage 50. An output of the finite element simulation is the estimated temperature field, which is a result of a simulation of heat diffusion in tissue.

In other embodiments, any suitable method may be used to solve the forward heat diffusion equation. For example, a data-driven surrogate model may be used to solve the forward heat diffusion equation, where the data-driven surrogate model is a model that is trained to quickly solve the heat diffusion equation. The data-driven surrogate model comprises a mapping from initial conditions and boundary conditions to a temperature field solution. The mapping may be parameterised by a neural network architecture. The mapping may be trained using many training pairs in which initial conditions and boundary conditions are paired with a corresponding temperature field solution. The training pairs may have been generated using a finite element method. At runtime, the data-driven surrogate model may very quickly predict the temperature field. In further embodiments, any suitable simulation of heat may be used.

In stage 52, the simulation comprises a simulation of heating in a generic tissue, for example a homogenous region of soft tissue. In other embodiments, the simulation may be tailored to a tissue type or anatomy of the tissue on which the ablation process is performed.

In an alternative variant of the method of FIG. 3, stage 50 comprises sub-stage 54 instead of sub-stage 52. At sub-stage 54, the simulation circuitry 34 uses a pre-defined analytic function to obtain the estimated temperature field. For example, the pre-defined analytic function may comprise a Gaussian function. The pre-defined analytic function may also be referred to as an analytic function expression.

Parameters of the finite element simulation may be based on the values for the heating parameters received at stage 50. In some embodiments, the pre-defined analytic function may be circularly symmetric. The pre-defined analytic function may be symmetric even if it is expected that heating is not symmetric.

In some circumstances, the use of a pre-defined analytic function may reduce the computing resources required to obtain the estimate of the temperature field when compared with use of a finite element simulation or other simulation.

The estimated temperature field provides expected temperatures given values for heating parameters, for example expected temperatures for the probe position, probe power and ablation time used to perform the ablation process. The estimating of the temperature field is independent of subsequent stages of FIG. 3.

In further embodiments, any suitable method may be used to obtain the estimate of the temperature field. For example, the estimated temperature field may be obtained from a look-up table. The estimated temperature field may be obtained from any suitable list, table, or function.

At stage 60, the correction circuitry 36 performs an optimization procedure to fit the estimate of the temperature field to the CT thermography image. The estimated temperature field is parameterized using one or more function parameters. For example, the function parameters may include a scale factor that is representative of a scale of the estimated temperature field and/or a shape parameter that is representative of a shape of the estimated temperature field. Any suitable number of function parameters may be used. An arbitrarily complex parameterization may be used.

In the optimization procedure, values for one or more function parameters of the estimated temperature field are optimized so that the estimated temperature field is as close as possible to the CT thermography image. A difference between the estimated temperature field and the observed CT thermography image is minimized. Any suitable optimization method may be used, for example any suitable off the shelf optimization algorithm. For example, a scale parameter may be optimized to scale the estimated temperature field.

The optimization procedure may result in an updated version of the estimated temperature field, in which function parameters of the estimated temperature field have been changed to obtain a better fit.

FIG. 3 illustrates an example of a Gaussian function 64 which is optimized to provide a best fit to a raw CT thermography image 62. The Gaussian function 64 is a three-dimensional Gaussian function, but is illustrated in two dimensions for ease of illustration.

The optimization procedure of stage 60 may reduce a difference between prediction and reality. In some embodiments, the optimization procedure of stage 60 may be omitted. In some circumstances, the optimization procedure of stage 60 may not be necessary to obtain accurate simulations.

In some embodiments, the optimization procedure of stage 60 is performed using the whole CT thermography image. In other embodiments, the correction circuitry 36 selects a part of the CT thermography image for use in the optimizing. The optimizing is based on the selected part of the CT thermography image rather than on the whole of the CT thermography image.

The selected part of the CT thermography image may comprise a selected subset of voxels of the CT thermography image. The subset of voxels may be based on box constraints, where the box constraints may comprise setting minimum and maximum voxel values and selecting only voxels that are between the minimum and maximum voxel values. The selecting of the part of the CT thermography image may comprise selecting a part of the CT thermography image in which there are large temperature values, indicating that that part of the CT thermography image includes tissue that is very hot. In some embodiments, the selecting of the part of the CT thermography image may comprise removing outlying values, which may be very high and/or very low temperature values.

At stage 70, the correction circuitry 36 uses the estimated temperature field that was output from stage 60 to process the CT thermography image to generate a corrected CT thermography image 82. The processing comprises performing a smoothing process to smooth the CT thermography image, and the corrected CT thermography image is a smoothed CT thermography image. In the embodiment of FIG. 3, the smoothing process comprises averaging across temperature iso-regions.

The smoothing that is performed at stage 70 may be described as an intelligent smoothing of the CT thermography image.

Figure 4:
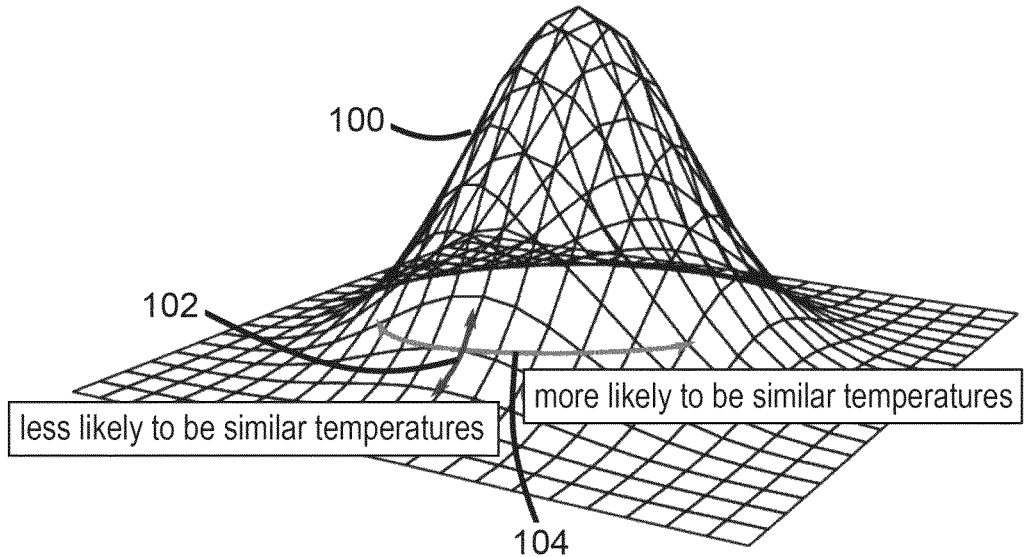
FIG. 4 is a plot of a Gaussian function used as an estimated temperature field.

FIG. 4 shows a graph 100 representing a Gaussian function that may be used as an estimated temperature field. The Gaussian function used as an estimate temperature field is three-dimensional, but is shown in two dimensions for ease of illustration. Arrow 102 shows a direction in which temperatures are expected to be dissimilar, based on the estimated temperature field. Arrow 104 shows a direction in which temperatures are expected to be similar, based on the estimated temperature field.

The smoothing of stage 70 uses the estimated temperature field to preferentially average between sub-regions of the CT thermography image that are expected to be at the same temperature. A sub-region may comprise a predetermined number of voxels. Sub-regions of the CT thermography image that are expected to be at similar temperature are averaged. Sub-regions of the CT thermography image that are expected to have different temperatures are not averaged. The smoothing is therefore anisotropic.

Any suitable smoothing method may be used. In the embodiment of FIG. 3 the smoothing method comprises using a spatially-dependent anisotropic smoothing kernel which preferentially smooths across regions with similar expected temperatures. A CT thermography image is written as I and an expected temperature from the estimated temperature field is written as T. A spatially-dependent anisotropic smoothing kernel g is convolved with the image I to obtain a smoothed CT thermography image, which may also be referred to as a corrected CT thermography image.

A smoothed CT thermography image $\widetilde{I(x)}$ may be expressed as:

$$\widetilde{I(x)} = \int_{y \in Y} I(y) g(x-y; x, y) dy,$$

where Y is the image domain and g is the smoothing kernel. x is a position at which an expected temperature T(x) is taken, which is then used to smooth other regions which are of similar temperatures.

The smoothing kernel g may be written as $$g(z; x, y) = A \exp(-\lambda |T(x) - T(y)| - z^T H z)$$

Where A, $\lambda$, and H are constants, and T is the expected temperature. The first term in the exponential weights regions with the same expected temperature more highly in the smoothing procedure. The second term in the exponential is a function of distance.

It may be considered that the smoothing procedure of FIG. 3 uses a similar mathematical framework to a traditional kernel-based smoothing or filtering method, but with an addition of the estimated temperature field to preferentially smooth sub-regions that are expected to be of similar temperatures.

In some embodiments, voxels outside a range of temperatures determined by the expected temperature distribution are ignored in the averaging procedure.

In some embodiments, a user may determine a degree of smoothing by providing an input value for the degree of smoothing. The degree of smoothing may be referred to as a user operable hyperparameter. The correction circuitry 36 may adjust the smoothing process in response to the user's input, for example by changing one or more of the constants used in the smoothing. In other embodiments, any suitable user input or inputs may be used to influence the processing of the CT thermography image at stage 60.

In another embodiment, the smoothing procedure uses an anisotropic kernel that depends on the expected temperature from the estimated temperature field. The kernel is constructed such that the CT thermography image is smoothed more heavily in directions orthogonal to the gradient of the estimated temperature field. Gradient can be understood as a difference in temperature between voxels. For example, if a first voxel has a high temperature and a second voxel has a low temperature, then there will be a strong temperature gradient between the two voxels. As a further example, if a first voxel has a first temperature and a second voxel has a similar, second temperature then there will be a smaller gradient between the two voxels.

Smoothing is not performed in directions having a high gradient, in which there is expected to be large temperature variation.

For example, the smoothed image $\widetilde{I(x)}$ may be expressed as:

$$\widetilde{I(x)} = \int_{y \in Y} I(y) g(x-y; x) dy$$

where Y is the image domain and g is the smoothing kernel.

A spatially-dependent anisotropic smoothing kernel may be defined as:

$$g(z;x) = \exp(-z^T H z)$$

where $$H = aI_n + b(\nabla T(x_0) \otimes \nabla T(x))$$

and where a and b are constants, $I_n$ is the identity matrix, and T is the expected temperature from the estimated temperature field.

In a further embodiment, the smoothing process uses a spatially-dependent isotropic smoothing kernel which is scaled according to an expected temperature.

For example, the smoothed image $\widetilde{I(x)}$ may be expressed as:

$$\widetilde{I(x)} = \int_{y \in Y} I(y) g(x-y;x) dy$$

where Y is the image domain.

The smoothing kernel g may be:

$$g(z;x) = A\exp(-z^T(1+\sigma(T(x)-T_0))\Sigma^{-1}z)$$

where A, $T_0$, and $\Sigma$ are constants, $\sigma$ is the sigmoid function, and T is the expected temperature. This is similar to regular Gaussian smoothing, but the magnitude of the variance depends on the expected temperature field, so that a small smoothing kernel is used in regions of expected high temperature and a large smoothing kernel in regions of low temperature.

In further embodiments, the processing of the CT thermography image at stage 70 comprises inference from a 3D conditional random field (CRF). A temperature field is predicted using a 3D CRF algorithm, where the 3D CRF algorithm takes into account both observed and predicted temperatures as well as a smoothness constraint and then solves an energy minimization problem to find an optimal temperature field.

In some embodiments, an energy function minimized by the 3D CRF takes the form:

$$E(y) = \sum_{i \in \Omega}(y_i - \overline{y}_i)^2 + \lambda_2 \sum_{i \in \Omega}(y_i - \hat{y}_i)^2 + \lambda_2 \sum_{(i,j) \in E}(y_i - y_j)^2$$

where y is the vector of all temperatures, $\Omega$ is the set of predicted temperatures, $\overline{y}_i$ is the expected temperature at index i, $\hat{y}_i$ is the observed temperature at index i, and E is the set of pairs of neighbouring predicted temperatures. This energy function is the combination of a data term based on the previously-computed expected temperature distribution, and a smoothness term.

In other embodiments, the processing of the CT thermography image at stage 70 comprises anisotropic diffusion. A diffusion coefficient of the anisotropic diffusion depends on the expected temperature obtained from the estimate temperature field.

For example, the image I may be evolved according to the following partial differential equation:

$$\frac{\partial I}{\partial t} = \nabla(c(T)\nabla I), \quad c(T) = \frac{1}{1 + \left(\frac{T}{K}\right)^2}$$

where T is the expected temperature, t is a pseudo-time variable, and K is a problem-dependent constant.

In further embodiments, any suitable method of processing the CT thermography image may be used at stage 70.

At stage 80, the correction circuitry 36 passes the corrected CT thermography image 82 to the display circuitry 38. The display circuitry 38 displays on the display screen 26, or on any suitable display, an image rendered from the corrected CT thermography image 82. In the corrected CT thermography image 82, a heated region 84 appears smoother and more continuous than in the original CT thermography image that was received at stage 40. Artefacts and/or noise may be removed.

FIG. 3 also shows a CT thermography image 90 that would be obtained if a naïve Gaussian averaging were to be performed instead of the processing performed in stage 70 of FIG. 3. The naïve Gaussian averaging does not take into account, for example, temperatures or temperature gradient. The naïve Gaussian averaging does not make use of any estimated temperature field. Unphysical artefacts remain in the CT thermography image 90.

By processing the CT thermography image in dependence on an estimate temperature field, the method of FIG. 3 takes advantage of knowledge of the underlying physical process of deposition of heat in tissue. Artefacts and/or noise may be removed. A poor signal-to-noise ratio of a thermography signal may be addressed by using physical priors for determining an averaging process. The removal of artefacts and noise may enable use of CT thermography to support thermal ablation procedures. The corrected CT thermography image may be easier for a user to interpret. The corrected CT thermography image may allow a user to assess heating provided by an ablation procedure.

In the embodiment of FIG. 3, a single CT thermography image is obtained from a pair of CT images comprising a pre-ablation image and a post-ablation image of the same anatomical region. The single CT thermography image is corrected by determining and fitting an estimated temperature field, and smoothing the CT thermography image in dependence on the estimated temperature field.

In other embodiments, multiple CT thermography measurements are obtained at distinct time points through a procedure, for example an ablation procedure. For example, a first CT thermography image may be obtained from a pre-ablation image and a first CT image obtained during the ablation, a second CT thermography image may be obtained from the pre-ablation image and a second CT image obtained later in the ablation than the first CT image, a third CT thermography image may be obtained from the pre-ablation image and a third CT image obtained later in the ablation than the second CT image; and a final CT thermography image may be obtained from the pre-ablation image and a final CT image obtained at the end of the ablation. In other embodiments, CT thermography images may be obtained from all possible pairs of CT images, which may be pre-ablation, peri-ablation or post-ablation. For example, if 4 CT images have been obtained, 6 possible thermography images may be obtained. In some embodiments, all available image pairs for a given time point may be averaged.

A temperature field is estimated using one of the estimation methods described above. The estimating of the temperature field may be based on a time to perform the entire ablation procedure.

The correction circuitry 36 fits the estimated temperature field to each of the CT thermography images to obtain a different scaling parameter with regard to each of the CT thermography images. The correction circuitry 36 then corrects one or more of the CT thermography images using the fitted temperature field.

In some circumstances, fitting to more than one image may have an effect of reducing noise.

In the embodiment of FIG. 3, a CT thermography image is received and is corrected. In other embodiments, a pair of measured CT images are received at stage 40. For example, the pair of measured CT images may comprise a pre-ablation image and a post-ablation image. A temperature field is estimated at stage 50 in a similar manner to the embodiment of FIG. 3, and may be fitted as described at stage 60 of FIG. 3. At stage 70, the correction circuitry 36 processes each CT image of the pair of CT images using the estimated temperature field to obtain from each CT image a respective corrected CT image. For example, the processing may comprise preferentially smoothing in accordance with a temperature and/or a temperature gradient. The correction circuitry 36 then subtracts the pair of corrected CT images to determine a corrected CT thermography image.

In other embodiments, any of the temperature field estimation methods or image processing methods described above may be applied to embodiments in which a pair of CT images are received instead of a CT thermography image.

In embodiments described above, a CT thermography image relating to an ablation procedure is processed. In other embodiments, a CT thermography image or pair of CT images relating to any suitable heating process in any human or animal subject may be processed to obtain a corrected CT thermography image.

In some embodiments, CT images used to obtain a CT thermography images may comprise cone-beam CT data that is normalised to Hounsfield units (HU).

In further embodiments, a process of smoothing based on an expected temperature distribution may be applied to any thermography method and to thermography images acquired in any suitable modality, for example to MR thermography. In MR thermography, the smoothing may be applied to a single image without a subtraction step. The expected temperature distribution may be obtained using any suitable method, for example any of the methods described above for obtaining an expected temperature field that are described above. The smoothing may be performed using any suitable method, for example any of the smoothing methods described above.

In embodiments described above, smoothing is performed on a 3D thermography images. In other embodiments, smoothing may be performed on 2D thermography images, for example on single slices. In such embodiments, the computing of the expected temperature field may still comprise a 3D calculation.

Certain embodiments provide a medical image processing apparatus comprising processing circuitry configured to: receive CT (computed tomography) thermography image for correction, estimate temperature field corresponding to the CT thermography image, correct the CT thermography image based on the temperature field.

The processing circuitry may be further configured to correct the CT thermography image by fitting the CT thermography image to the temperature field and averaging the fitted CT thermography image in sub region.

Certain embodiments provide a medical image processing apparatus comprising processing circuitry configured to: (i) receive measured CT thermography data; (ii) receive parameters defining an expected temperature change, such as probe position, probe power, and ablation time; (iii) determine an expected temperature distribution using parameters received in (ii); (iv) smooth the original CT thermography received in (i) using the expected temperature determined in (iii).

The expected temperature distribution may be given by an analytic function expression.

The expected temperature distribution may be given by the result of a simulation of heat diffusion in tissue.

The expected temperature distribution may be obtained from a look-up table.

The determination of expected temperature may comprise optimisation of the function parameters to minimise the difference between the expected temperature and the observed CT Thermography.

Only a subset of voxels may be used in the optimisation based on box constraints on the original CT and CT thermography values.

The CT thermography processing may comprise a spatially-dependent averaging procedure in which the averaging kernel depends on the expected temperature distribution.

Voxels outside bounds determined by the expected temperature distribution may be ignored in the averaging procedure.

The CT thermography processing may comprise a spatially-dependent isotropic smoothing kernel which is scaled according to the expected temperature.

For example, the smoothed image $\widetilde{I(x)}$ may be expressed as:

$$\widetilde{I(x)} = \int_{y \in Y} I(y) g(x-y;x) dy, \; g(z;x_0) = A \exp(-z^T (1 + \sigma(T(x_0) - T_0)) \Sigma^{-1} z)$$

where Y is the image domain, A, $T_0$, and $\Sigma$ are constants, $\sigma$ is the sigmoid function, and T is the expected temperature. This is similar to regular Gaussian smoothing, but the magnitude of the variance depends on the expected temperature field, so that a small smoothing kernel is used in regions of expected high temperature and a large smoothing kernel in regions of low temperature.

The CT thermography processing may comprise a spatially-dependent anisotropic smoothing kernel which preferentially smooths orthogonal to the gradient of the expected temperature.

For example, a spatially-dependent anisotropic kernel g(x) could be defined as:

$$g(z;x_0) = \exp(-z^T H z), \; H = aI + b(\nabla T(x_0) \otimes \nabla T(x_0))$$

Where a, b are constants, I is the identity matrix. This anisotropic kernel is constructed such that the thermography image is smoothed more heavily in directions orthogonal to the gradient of the expected temperature field.

The CT thermography processing may comprise a spatially-dependent anisotropic smoothing kernel which preferentially smooths across regions with similar expected temperatures.

For example, the smoothed image $\widetilde{I(x)}$ may be expressed as:

$$\widetilde{I(x)} = \int_{y \in Y} I(y) g(x-y;x,y) dy, \; g(z;x_0,y) = A \exp(-\lambda |T(x_0) - T(y)| - z^T H z)$$

where Y is the image domain, A, $\lambda$, and H are constants, and T is the expected temperature. The first term in the exponential weights regions with the same expected temperature more highly in the smoothing procedure.

The CT thermography processing may comprise inference from a 3D conditional random field (CRF).

The energy function minimised by this CRF may take the form:

$$E(y) = \sum_{i \in \Omega} (y_i - \bar{y}_i)^2 + \lambda_2 \sum_{i \in \Omega} (y_i - \hat{y}_i)^2 + \lambda_2 \sum_{(i,j) \in E} (y_i - y_j)^2$$

where y is the vector of all temperatures, $\Omega$ is the set of predicted temperatures, $\bar{y}_i$ is the expected temperature at index i, $\hat{y}_i$ is the observed temperature at index i, and E is the set of pairs of neighbouring predicted temperatures. This energy function is the combination of a data term based on the previously-computed expected temperature distribution, and a smoothness term.

The CT thermography processing may comprise anisotropic diffusion, where the diffusion coefficient depends on the expected temperature.

In the anisotropic diffusion smoothing method, the image I may be evolved according to the following partial differential equation:

$$\frac{\partial I}{\partial t} = \nabla(c(T)\nabla I), \; c(T) = \frac{1}{1 + \left(\frac{T}{K}\right)^2}$$

where T is the expected temperature, t is a pseudo-time variable, and K is a problem-dependent constant.

A data-driven surrogate model may be used to solve the forward heat diffusion equation.

A finite element method may be used to solve the forward heat diffusion equation.

Multiple CT thermography measurements may be obtained at distinct time points during the procedure, and the expected temperature field for the final time point is fitted to all measurements through different scaling parameters.

The degree of smoothing may be a user operable hyperparameter.

Certain embodiments provide a medical image processing apparatus comprising processing circuitry configured to: (i) receive a pair of measured CT images; (ii) receive parameters defining an expected temperature change, such as probe position, probe power, and ablation time; (iii) determine an expected temperature distribution using parameters received in (ii); (iv) smooth the original CT data received in (i) using the expected temperature determined in (iii), prior to subtraction to determine the thermography image.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus, comprising: processing circuitry configured to:

receive a thermography image, or a pair of medical images from which a thermography image is obtainable;

estimate a temperature field corresponding to the thermography image or the pair of medical images, by fitting the estimated temperature field to the thermography image by optimizing one or more function parameters of the estimated temperature field; and generate a corrected thermography image based on the thermography image or the pair of medical images and on the estimated temperature field, by performing smoothing of the thermography image or the pair of medical images by determining a gradient of temperature in the estimated temperature field, and performing a smoothing procedure comprising smoothing in a direction orthogonal to the gradient of temperature.

2. The apparatus according to claim 1, wherein the thermography image comprises a subtraction image obtained by subtracting a first CT image acquired at a first time and a second CT image acquired at a second, different time.

3. The apparatus according to claim 1, wherein the pair of medical images comprises a first CT image acquired at a first time and a second CT image acquired at a second, different time, and wherein the processing circuitry is further configured to generate the corrected thermography image by generating a corrected first CT image based on the estimated temperature field;

generating a corrected second CT image based on the estimated temperature field; and subtracting the corrected first CT image and the corrected second CT image to obtain the corrected thermography image.

4. The apparatus according to claim 1, wherein the processing circuitry is further configured to optimize the one or more function parameters by minimizing a difference between the estimated temperature field and the thermography image or the pair of medical images.

5. The apparatus according to claim 1, wherein the processing circuitry is further configured to estimate the temperature field by selecting a part of the image for use in the optimizing, and performing the optimizing based on the selected part of the image.

6. The apparatus according to claim 1, wherein the processing circuitry is further configured to generate the corrected thermography image by smoothing the thermography image or smoothing each medical image of the pair of medical images, and wherein a degree of smoothing used in the smoothing of the thermography image or the pair of medical images is selected by a user.

7. The apparatus according to claim 1, wherein the thermography image or the pair of medical images relate to an ablation process performed on tissue of a subject.

8. The apparatus according to claim 1, wherein the processing circuitry is further configured to estimate the temperature field based on at least one heating parameter related to an application of heat to tissue imaged in the thermography image or the pair of medical images.

9. The apparatus according to claim 8, wherein the at least one heating parameter comprises at least one of a probe position, a probe power, a probe parameter, an ablation time, an electric field parameter, a rate of heat deposition, a tissue type, or a tissue geometry.

10. The apparatus according to claim 1, wherein the processing circuitry is further configured to estimate the temperature field using an analytic function expression.

11. The apparatus according to claim 1, wherein the processing circuitry is further configured to estimate the temperature field using a simulation of heat diffusion.

12. The apparatus according to claim 11, wherein the simulation of the heat diffusion uses at least one of a finite element method or a data-driven surrogate model.

13. The apparatus according to claim 1, wherein the processing circuitry is further configured to estimate the temperature field using a look-up table.

14. The apparatus according to claim 1, wherein the processing circuitry is further configured to generate the corrected thermography image by applying to the thermography image or the pair of medical images at least one of:
   a spatially-dependent averaging procedure;
   a spatially-dependent isotropic smoothing procedure;
   a spatially-dependent anisotropic smoothing procedure;
   a 3D conditional random field inference procedure; or
   anisotropic diffusion.

15. The apparatus according to claim 1, wherein the processing circuitry is further configured to receive a thermography image and at least one further thermography image, and estimate the temperature field by fitting the temperature field to the thermography image and to the further thermography image.

16. The apparatus according to claim 15, wherein the thermography image and the further thermography image are representative of different times, and
   the fit the temperature field to the thermography image and to the further thermography image by determining a first value for at least one function parameter of the estimated temperature field in relation to the thermography image and a second, different value for the at least one function parameter of the estimated temperature field in relation to the further thermography image.

17. The apparatus according to claim 1, wherein the thermography image is a magnetic resonance (MR) thermography image and the corrected thermography image is a corrected MR thermography image.

18. A medical image processing method, comprising:
   receiving a thermography image, or a pair of medical images from which a thermography image is obtainable;
   estimating a temperature field corresponding to the thermography image or the pair of medical images, by fitting the estimated temperature field to the thermography image by optimizing one or more function parameters of the estimated temperature field; and
   generating a corrected thermography image based on the thermography image or the pair of medical images and on the estimated temperature field, by performing smoothing of the thermography image or the pair of medical images by determining a gradient of temperature in the estimated temperature field, and performing a smoothing procedure comprising smoothing in a direction orthogonal to the gradient of temperature.

* * * * *